US012612600B2

(12) United States Patent
Gong et al.

(10) Patent No.: US 12,612,600 B2
(45) Date of Patent: Apr. 28, 2026

(54) METHODS FOR PREPARING MESENCHYMAL STEM CELLS

(71) Applicant: ALLIFE MEDICINE (BEIJING) LIMITED, Beijing (CN)

(72) Inventors: Shixin Gong, Beijing (CN); Yuchun Gu, Beijing (CN); Nan Li, Beijing (CN); Qinqing Peng, Beijing (CN); Lida Wu, Beijing (CN)

(73) Assignee: ALLIFE MEDICINE (BEIJING) LIMITED, Beijing (CN)

( * ) Notice: Subject to any disclaimer, the term of this patent is extended or adjusted under 35 U.S.C. 154(b) by 0 days.

(21) Appl. No.: 19/093,919

(22) Filed: Mar. 28, 2025

(65) Prior Publication Data

US 2025/0250543 A1 Aug. 7, 2025

Related U.S. Application Data

(63) Continuation of application No. PCT/CN2023/074764, filed on Feb. 7, 2023.

(30) Foreign Application Priority Data

Sep. 28, 2022 (CN) .......................... 202211194577.1

(51) Int. Cl.
*C12N 5/0775* (2010.01)

(52) U.S. Cl.
CPC ........ *C12N 5/0665* (2013.01); *C12N 2500/25* (2013.01); *C12N 2500/32* (2013.01); *C12N 2500/38* (2013.01); *C12N 2500/84* (2013.01); *C12N 2501/11* (2013.01); *C12N 2501/155* (2013.01); *C12N 2501/999* (2013.01); *C12N 2506/025* (2013.01)

(58) Field of Classification Search
None
See application file for complete search history.

(56) References Cited

U.S. PATENT DOCUMENTS

| | | | |
|---|---|---|---|
| 10,745,670 | B2 | 8/2020 | Liu et al. |
| 2018/0195046 | A1 | 7/2018 | Deng et al. |
| 2018/0201904 | A1 | 7/2018 | Liu et al. |
| 2020/0131473 | A1 | 4/2020 | Costanzo et al. |
| 2022/0145264 | A1 | 5/2022 | Liu et al. |
| 2024/0191205 | A1 | 6/2024 | Wu et al. |

FOREIGN PATENT DOCUMENTS

| | | | |
|---|---|---|---|
| CN | 101402943 | A | 4/2009 |
| CN | 104204193 | A | 12/2014 |
| CN | 107904202 | A | 4/2018 |
| CN | 108478599 | A | 9/2018 |
| CN | 109844093 | A | 6/2019 |
| CN | 109913494 | A | 6/2019 |
| CN | 110713973 | B | 5/2021 |
| CN | 114540282 | A | 5/2022 |
| CN | 114762725 | A | 7/2022 |
| CN | 114774365 | A | 7/2022 |
| CN | 111944035 | B | 8/2022 |
| CN | 115247151 | A | 10/2022 |
| CN | 115247152 | A | 10/2022 |
| CN | 115305234 | A | 11/2022 |
| WO | 2021106765 | A1 | 6/2021 |

OTHER PUBLICATIONS

Jang et al., (May 10, 2022) Induction of human trophoblast stem-like cells from primed pluripotent stem cells. PNAS, 119(20): e2115709119 (Year: 2022).*
Wang et al., (Feb. 2016) Immune modulatory mesenchymal stem cells derived from human embryonic stem cells through a trophoblast-like stage. Stem Cells, 34: 380-391 (Year: 2016).*
Notification to Grant Patent Right for Invention in Chinese Application No. 202211194577.1 mailed on Dec. 28, 2022, 4 pages.
First Office Action in Chinese Application No. 202211194577.1 mailed on Nov. 16, 2022, 16 pages.
Zhang, Chongben, Type I Diabetes, Hubei Science and Technology Press, p. 201, 2017.
Wang, XiaoFang et al., Immune Modulatory Mesenchymal Stem Cells Derived from Human Embryonic Stem Cells Through a Trophoblast-Like Stage, Stem Cells, 34: 380-391, 2015.
Gao, Xuefei et al., Establishment of porcine and human expanded potential stem cells, Nature Cell Biology, 21: 687-699, 2019.

(Continued)

*Primary Examiner* — Kara D Johnson
(74) *Attorney, Agent, or Firm* — PORUS IP LLC

(57) ABSTRACT

A method for preparing mesenchymal stem cells (MSCs) is provided. The method includes providing expanded potential stem cells or a first cell culture including the expanded potential stem cells; culturing the expanded potential stem cells or the first cell culture in a trophoblast stem cell (TSC) differentiation medium to obtain trophoblast stem cells or a second cell culture including the trophoblast stem cells; culturing the trophoblast stem cells or the second cell culture in a mesenchymal stem cell (MSC) differentiation medium to obtain mesenchymal stem cells or a third cell culture including the mesenchymal stem cells; and passaging the mesenchymal stem cells or the third cell culture in an MSC expansion medium while maintaining characteristics of the mesenchymal stem cells.

10 Claims, 7 Drawing Sheets

(56)             References Cited

OTHER PUBLICATIONS

Zhang, Kun, Study of mesenchymal stem cell preparation methods at scale for human hematopoietic stem cell sources, Chinese Excellent Master's Thesis Full Text Database, Medical and Health Technology Collection, pp. 1-78, 2022.

International Search Report in PCT/CN2023/074764 mailed on Jun. 18, 2023, 7 pages.

Written Opinion in PCT/CN2023/074764 mailed on Jun. 18, 2023, 8 pages.

Chen, Zhenzhen et al., Progress on derivation of human embryonic stem cell, Chinese Bulletin of Life Sciences, 30 (8): 906-910, 2018.

Ying Lei et al., Paracrine FGFs Target Skeletal Muscle to Exert Potent Anti-hyperglycemic Effects, Nature Communications, 2021, 14 pages.

* cited by examiner

Adipogenic
differentiation

Osteogenic
differentiation

Chondrogenic
differentiation a                    b                    c

1

METHODS FOR PREPARING MESENCHYMAL STEM CELLS

CROSS-REFERENCE TO RELATED APPLICATIONS

This application is a Continuation of International Application No. PCT/CN2023/074764, filed Feb. 7, 2023, which claims priority to Chinese Patent Application No. 202211194577.1, filed on Sep. 28, 2022, the entire contents of which are incorporated herein by reference.

TECHNICAL FIELD

The present disclosure relates to the field of cell biology, and particularly relates to a method for preparing mesenchymal stem cells.

BACKGROUND

Mesenchymal stem cells (MSCs) are widely found in a variety of human tissues and have the potential for multi-directional differentiation, hematopoietic support, promotion of stem cell implantation, immune modulation, and self-replication.

The mesenchymal stem cells can be isolated from a variety of human tissues (e.g., bone marrow, adipose tissue, umbilical cord blood, peripheral blood, neonatal tissues, placenta, etc.). However, the number of the mesenchymal stem cells that can be obtained from human tissues is limited and invasive procedures are required to isolate the mesenchymal stem cells, which poses a risk to the donor.

The prior art typically employs a method of preparing the mesenchymal stem cells by inducing differentiation of human pluripotent stem cells into the mesenchymal stem cells. However, this method suffers from long cycle time, low yield, and contamination by xeno pathogens, which is detrimental to the commercialization of the mesenchymal stem cells as cell therapeutic agents.

Therefore, it is desired to provide a method of preparing the mesenchymal stem cells, capable of shortening the preparation cycle and increasing the yield and quality of the mesenchymal stem cells.

SUMMARY

The present disclosure provides a method for preparing mesenchymal stem cells. The method includes the steps of a) providing expanded potential stem cells or a first cell culture including the expanded potential stem cells; b) culturing the expanded potential stem cells or the first cell culture in a trophoblast stem cell (TSC) differentiation medium to obtain trophoblast stem cells or a second cell culture including the trophoblast stem cells, the TSC differentiation medium including a basal medium, 2-mercapto-ethanol, serum replacement, insulin-transferrin-selenium-X supplement (ITS-X supplement), L-ascorbic acid-2-phosphate (L-AA-pi), epidermal growth factor (EGF), glycogen synthase kinase 3 beta (GSK3B) receptor inhibitor CHIR99021, anaplastic lymphoma kinase (ALK) 4/5/7 inhibitor A83-01, ALK5 inhibitor SB431542, valproic acid, Rho-associated protein kinase (ROCK) inhibitor Y27632, and bone morphogenetic protein 4 (BMP4), wherein the basal medium is an essential medium or a medium prepared by mixing dulbecco's modified eagle medium/nutrient mixture F-12 (DMEM/F-12 medium) and iscove's modified dulbecco's medium (IMDM medium) at a ratio of 1:1; c) culturing the trophoblast stem cells or the second cell culture in a mesenchymal stem cell (MSC) differentiation medium to obtain mesenchymal stem cells or a third cell culture including the mesenchymal stem cells, the MSC differentiation medium including minimum essential medium α (α-MEM) medium, 1×non-essential amino Acids (1×NEAA) cell culture supplement, 1×alanyl-glutamine (1×GlutaMax) supplement, 2-mercaptoethanol, fetal bovine serum, and human platelet lysate; and d) passaging the mesenchymal stem cells or the third cell culture in an MSC expansion medium while maintaining characteristics of the mesenchymal stem cells, the MSC expansion medium including α-MEM medium, 1×NEAA cell culture supplement, 1×GlutaMax supplement, 0.1 mM 2-mercaptoethanol, 5% fetal bovine serum, and 5% human platelet lysate. The mesenchymal stem cells obtained in the step c) and the step d) are mesenchymal stem cells expressing cell surface markers CD44, CD73, CD90, CD105, CD166; and in mesenchymal stem cells at a 16th passage or later, a proportion of the mesenchymal stem cells expressing the cell surface markers CD44, CD73, CD90, CD105, and CD166 is not less than 95%.

In some embodiments, the step b) may be performed for 4-8 days.

In some embodiments, the step b) may be performed for 6 days.

In some embodiments, the step c) may include: subjecting the trophoblast stem cells or the second cell culture to an MSC differentiation culture for 5-7 days to obtain P1 generation cells, and continually subjecting the P1 generation cells to the MSC differentiation culture for 6-9 days to obtain the mesenchymal stem cells or the third cell culture. The step d) may include: subjecting the P1 generation cells to an MSC expansion culture to obtain P2 generation cells, subjecting the P2 generation cells to the MSC expansion culture to obtain P3 generation cells, subjecting the P3 generation cells to the MSC expansion culture to obtain P4 generation cells, and continually subjecting the P4 generation cells to the MSC expansion culture every 3 days.

In some embodiments, the step c) may include: subjecting the trophoblast stem cells or the second cell culture to the MSC differentiation culture for 5 days to obtain the P1 generation cells, and continually subjecting the P1 generation cells to the MSC differentiation culture for 7 days to obtain the mesenchymal stem cells or the third cell culture.

In some embodiments, the TSC differentiation medium may include the basal medium, 0.1 mM 2-mercaptoethanol, 20% serum replacement, 1% ITS-X supplement, 1.5 µg/ml L-AA-pi, 50 ng/ml EGF, 2 µM CHIR99021, 0.5 µM A83-01, 1 µM SB431542, 0.8 mM valproic acid, 5 µM Y27632, and 10 ng/mL BMP4.

In some embodiments, the MSC differentiation medium may include α-MEM medium, the 1×NEAA cell culture supplement, the 1×GlutaMax supplement, 0.1 mM 2-mercaptoethanol, 5% fetal bovine serum, and 5% human platelet lysate.

In some embodiments, the trophoblast stem cells obtained in the step b) may be trophoblast stem cells expressing cell surface markers GATA3 and KRT7.

In some embodiments, the MSCs obtained in the step c) and the step d) may be pluripotent mesenchymal stem cells capable of differentiating into adipocytes, osteocytes, chondrocytes, myocytes, neuronal cells, and cardiomyocytes.

In some embodiments, the mesenchymal stem cells obtained in the step c) and the step d) may be mesenchymal stem cells expressing cell surface markers HLADR, CD34, and CD45. In mesenchymal stem cells at a 16th passage or later, a proportion of the mesenchymal stem cells expressing the cell surface markers HLADR, CD34, and CD45 may be not greater than 3%.

The present disclosure also provides mesenchymal stem cells. The mesenchymal stem cells may be prepared by the method described above.

BRIEF DESCRIPTION OF THE DRAWINGS

The present disclosure will be further illustrated by way of exemplary embodiments, which will be described in detail through the accompanying drawings.

DETAILED DESCRIPTION

Figure 1:
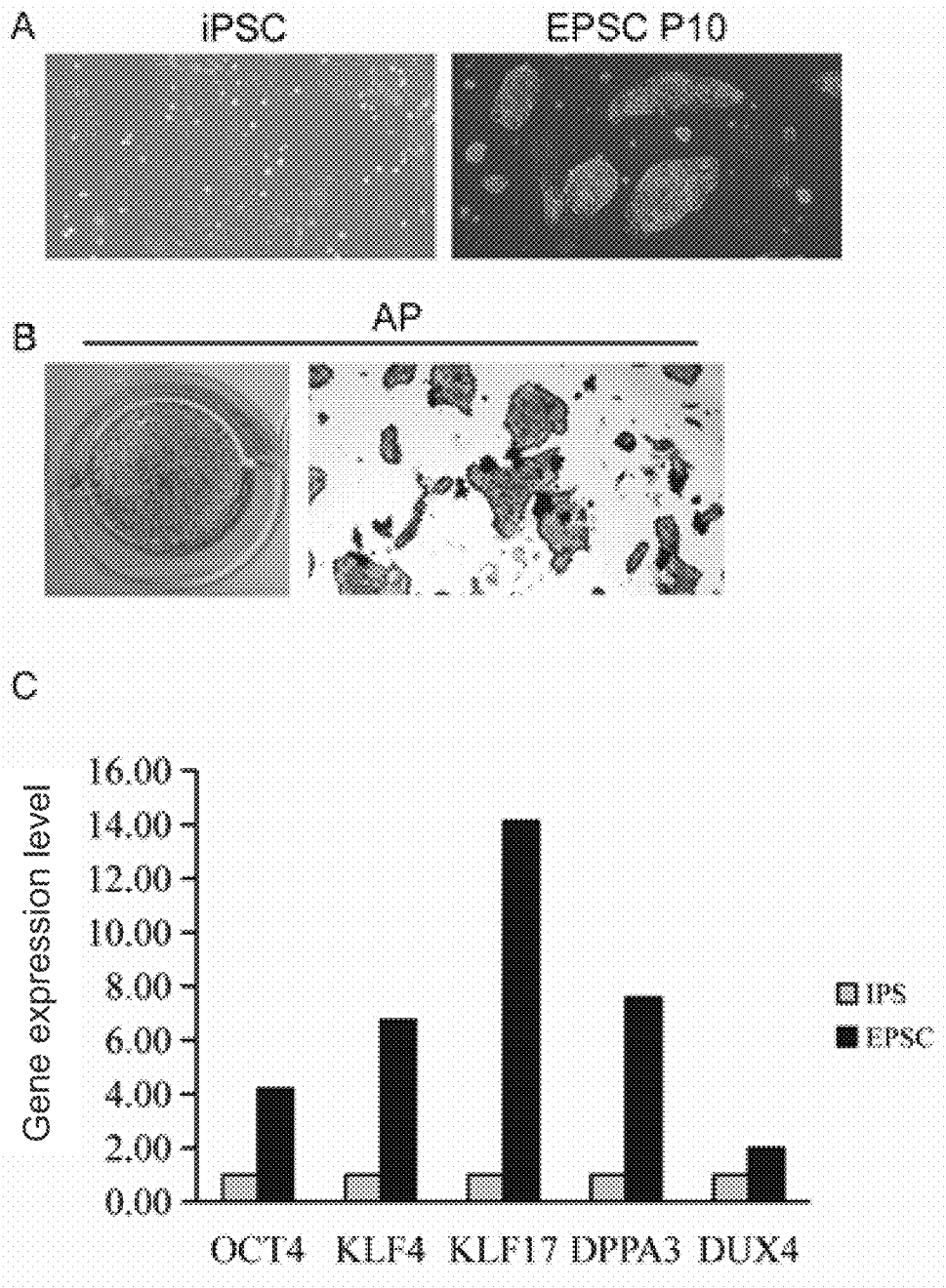
FIG. 1 shows a morphology image, a staining image, and a gene expression profile graph of the prepared expanded potential stem cells according to some embodiments of the present disclosure.

The following is a further description of the present disclosure in conjunction with embodiments, and the following descriptions are only better embodiments of the present disclosure, and are not intended to limit the present disclosure in any other form, and any skilled person familiar with the art may utilize the technical contents revealed above to change to equivalent embodiments with equivalent variations. Any simple modification or equivalent change of the following embodiments based on the technical substance of the present disclosure without departing from the content of the present disclosure falls within the scope of the present disclosure.

All technical and scientific terms used in the present disclosure have the meanings commonly understood by a person of ordinary skill in the art, unless otherwise indicated.

The term "or" refers to a single element of an enumerated optional element, unless the context clearly indicates otherwise.

The term "comprising" or "including" means including an element, integer, or step described, but not excluding any other element, integer, or step. When "comprising" or "including" is used, unless otherwise specified, the use of "comprising" or "including" also covers situations consisting of elements, integers, or steps as described.

The term "stem cell" refers to an undifferentiated or insufficiently differentiated cell that is capable of self-renewing, i.e., producing more cells identical to itself, and of differentiating into two or more types of mature cells. Based on the source of stem cells, stem cells may be categorized into embryonic stem cells (ESCs) and adult stem cells (ASCs). The embryonic stem cells may be derived from early animal embryos, such as the inner cell mass of blastomeres (i.e., early embryos). The embryonic stem cells have totipotency, i.e., the ability to differentiate into every cell type in the body. The adult stem cells are found in various organs and tissues of an adult body. The adult stem cells are pluripotent, i.e., the ability to differentiate and replace cells of a tissue in which they are found.

The term "induced pluripotent stem cell (iPSC)" refers to stem cells with totipotency or pluripotency obtained from certain adult cells (e.g., fibroblasts) by artificially inducing the expression of certain genes. In some embodiments, iPSCs are obtained by transfecting certain stem cell-related genes into non-pluripotent cells (e.g., adult fibroblasts). Transfection may be achieved by viral transduction using a virus (e.g., retrovirus or lentivirus). For example, genes used for transfection include transcription factors (TF) Oct4, Sox2, Klf4, and c-Myc, and simultaneous transfection of other genes has the potential to improve induction efficiency. As another example, somatic cells are transformed by a lentiviral system employing Oct4, Sox2, Nanog, and Lin28 genes. Induced expression genes in obtaining iPSCs include Oct-3/4, certain members of the Sox gene family (e.g., Sox1, Sox2, Sox3, and Sox15), certain members of the Klf family (e.g., Klf1, Klf2, Klf4, and Klf5), certain members of the Myc family (e.g., C-myc, L-myc, and N-myc), Nanog, Lin28, Tert, Fbx15, ERas, ECAT15-1, ECAT15-2, Tcl1, β-Catenin, ECAT1, Esg1, Dnmt3L, ECAT8, Gdf3, Fth117, Sal14, Rex1, UTF1, Stella, Stat3, Grb2, Prdm14, Nr5a1, Nr5a2, E-cadherin, and so on, or any combination thereof. Various reagents for the preparation of iPSCs such as reprogramming vectors, expression cassettes, culture media, etc. are already commercially available. Commercially available iPSCs are also available from the market. In some embodiments, the iP SC further includes a human induced pluripotent stem cell (hiPSC). The hiPSC refers to iPSC induced from human cells.

The term "expanded potential stem cells (EPSCs)" has "naïve" or basal characteristics and has the potential to differentiate into extraembryonic cell lineages (e.g., trophoblasts in the yolk sac and extraembryonic endoderm) and potential of intrinsic embryonic cells derived from the inner cell mass of the blastocyst. Not only can EPSCs develop into any type of cell, but their developmental potential exceeds that of embryonic stem cells (ESCs) and induced pluripotent stem cells (IPSCs). EPSCs may be used for research and development, such as disease modeling, therapeutic screening, toxicity testing, genetic disease research, and reproductive biology research. EPSCs may also be used to generate functional cells in vitro. Currently, EPSCs have been successfully differentiated into pancreatic cells, neurons, T cells, and many other cell types. EPSCs may be prepared using methods reported in the literature, e.g., using the method in U.S. Pat. No. 10,745,670B2. The cell surface markers of EPSCs and iPSCs are similar, and thus EPSC identification also uses iPSC stemness genes, for example, ESRG, OCT4, SOX2, NANOG, LIN28A, POU5F1, etc. In the present disclosure, the presence or absence of EPSCs is identified by detecting the expression of ESRG, OCT4, SOX2, and NANOG on the cell surface.

The term "mesenchymal stem cells (MSCs)" usually refers to a class of pluripotent stem cells with differentiation potential. It meets the following definitions of the International Society for Cellular Therapy (ISCT): 1) MSCs may show colony-adherent growth; and 2) cell surfaces of MSCs express the markers CD105, CD73, and CD90, and do not express endothelial, hematopoietic, or immune cell markers, such as CD45, CD34, CD14, CD11b, CD79a, CD19, and HLA-DR. MSCs may be obtained in different tissues such as adipose, bone marrow, dental pulp, umbilical cord, etc., and by induced differentiation of ESCs or iPSCs. For example, the mesenchymal stem cells of the present disclosure are prepared by induced differentiation of EPSCs by a specific culture medium.

The term "trophoblast stem cells (TSCs)" is used to describe the progenitor cells of placental tissue cells, which progressively differentiate into trophoblast precursor cells, chorionic trophoblast, syncytiotrophoblast, and multinucleated giant cells. The trophoblast stem cells may be obtained directly from embryonic trophoblastic ectoderm or by induced differentiation of embryonic stem cells through spontaneous differentiation, gene knockout, and isolation of embryoid bodies. However, the cellular heterogeneity of the trophoblast stem cells obtained through spontaneous differentiation is high and not easily controlled. The knockout pathway only reflects changes in the expression of partial signature genes during cell differentiation. Caroline Kubaczka et al. completely overcame the unique epigenetic barrier consisting of DNA methylation and histone modification by transiently overexpressing the key regulators Tfap2c, Gata3, Eomes, and Ets2 of the trophoblast in mouse embryonic fibroblasts, and the induced trophoblast stem cells are capable of self-renewal that are virtually identical to blastula-derived trophoblast stem cells in terms of morphology, marker gene expression, and methylation patterns.

The term "significant" means a range of a quantity, level, value, number, frequency, percentage, scale, size, volume, weight, or length or events that are readily detectable by one or more standard methods. In one embodiment, an event is significant if the chance of it occurring is greater than 80%, 85%, 90%, 95%, 98%, 99%, 99.9%, 99.99%, 99.999%, 99.999%, or higher. The term "insignificant" and equivalent refer to a range of quantity, level, value, number, frequency, percentage, scale, size, volume, weight, or length or events that are not readily detectable or undetectable by a standard method. In one embodiment, an event is insignificant if the chance of it occurring is less than 5%, 4%, 3%, 2%, 1%, 0.1%, 0.01%, 0.001%, or less.

Currently, mesenchymal stem cells are commonly prepared by methods of inducing human pluripotent stem cells to differentiate into mesenchymal stem cells. However, the described method has problems such as long cycle time, low yield, and contamination by xeno pathogens, which are not conducive to the commercialization of MSCs as cell therapeutic agents. For example, the patent application publication CN110713973B discloses sequentially inducing the differentiation of pluripotent stem cells into precursor mesenchymal stem cells and mature mesenchymal stem cells, with a differentiation time of up to 30 days. Xiaofang Wang et al. (Immune modulatory mesenchymal stem cells derived from human embryonic stem cells through a trophoblast-like stage) obtained MSCs by inducing trophoblast-like stem cell differentiation, and although the differentiation time was shortened, the subsequent passaging time was about 10 days, the cell proliferation was slow, and the cells began to exhibit senescence after passaging 5 generations. The patent application publication CN114540282A discloses inducing the differentiation of MSCs by forming the iPSCs into a mimic embryoid body, which is a more complicated differentiation scheme, and the finally obtained MSCs may have low purity. At present, there is also no reports in the literature on the preparation of MSCs from EPSCs differentiation.

In order to be able to solve the above problem, the present disclosure provides a method for preparing mesenchymal stem cells. The method may include a) providing expanded potential stem cells or a first cell culture including the expanded potential stem cells; b) culturing the expanded potential stem cells or the first cell culture in a trophoblast stem cell (TSC) differentiation medium to obtain trophoblast stem cells or a second cell culture including the trophoblast stem cells; c) culturing the trophoblast stem cells or the second cell culture in a mesenchymal stem cell (MSC) differentiation medium to obtain mesenchymal stem cells or a third cell culture including the mesenchymal stem cells; and d) passaging the mesenchymal stem cells or the third cell culture in an MSC expansion medium while maintaining characteristics of the mesenchymal stem cells.

The cell culture method is a technique of growing, proliferating, or differentiating cells in an artificial environment.

Cell culture is a system of cells that are grown and maintained in an artificial environment and their media. For example, the first cell culture includes the expanded potential stem cells and a medium corresponding to the expanded potential stem cells (e.g., E8 complete medium). As another example, the second cell culture includes the trophoblast stem cells and a medium corresponding to the trophoblast stem cells (e.g., the trophoblast stem cell differentiation medium). As yet another example, the third cell culture includes the mesenchymal stem cells and a medium corresponding to the mesenchymal stem cells (e.g., the MSC differentiation medium or the MSC expansion medium).

In some embodiments, the cell culture further includes a supporting matrix. The supporting matrix may be used to help cells adhere to a wall or form a three-dimensional structure. Exemplary supporting matrix includes collagen, matrigel, etc., or any combination thereof.

The TSC differentiation medium is used for culturing the expanded potential stem cells to obtain the trophoblast stem cells. The TSC differentiation medium may include a basal medium, 2-mercaptoethanol, serum replacement, insulin-transferrin-selenium-X supplement (ITS-X supplement), L-ascorbic acid-2-phosphate (L-AA-pi), epidermal growth factor (EGF), glycogen synthase kinase 3 beta (GSK3B) receptor inhibitor CHIR99021, anaplastic lymphoma kinase (ALK) 4/5/7 inhibitor A83-01, ALK5 inhibitor SB431542, valproic acid, Rho-associated protein kinase (ROCK) inhibitor Y27632, and bone morphogenetic protein 4 (BMP4), and so on, or any combination thereof. The serum replacement may include recombinant proteins, growth factors and hormones, antioxidants, vitamins, cofactors, etc. The recombinant proteins may include such as recombinant human albumin, transferrin, etc., which replace natural proteins in traditional serum to support cell adhesion and proliferation. The growth factors may include such as insulin-like growth factor (IGF), epidermal growth factor (EGF), etc., which promote cell division and pluripotency maintenance. The antioxidants may include such as β-mercaptoethanol (β-ME) or similar components, protecting cells from oxidative stress damage. The vitamins may include such as vitamin B group and vitamin C derivatives (e.g., L-ascorbic acid-2-phosphate), etc., supporting cellular metabolism and collagen synthesis. The cofactors may include such as selenium, zinc, copper, etc., acting as enzymatic cofactors to enhance cellular functions. In some embodiments, the serum replacement may be KnockOut™ serum replacement. For example, the TSC differentiation medium includes the basal medium, 0.1 mM 2-mercaptoethanol, 20% KnockOut™ serum replacement, 1% ITS-X supplement, 1.5 µg/ml L-AA-pi, 50 ng/ml epidermal growth factor, 2 µM CHIR99021, 0.5 µM A83-01, 1 UM SB431542, 0.8 mM valproic acid, 5 µM Y27632, and 10 ng/ml BMP4.

The basal medium is a basic substance that provides cellular nutrition and induces cell proliferation. For example, the basal medium includes carbohydrates, nitrogen-containing substances, inorganic salts (including trace elements), vitamins, water, etc. Merely by way of example, the basal medium is an essential medium or a medium prepared by mixing Dulbecco's modified eagle medium/ nutrient mixture F-12 (DMEM/F-12 medium) and Iscove's modified dubecco's medium (IMDM medium) at a ratio of 1:1. The essential medium may include a basal medium. The basal medium may include such as DMEM/F12, which provides glucose, amino acids, inorganic salts, and other essential nutrients. In some embodiments, the essential medium may be essential 6™ medium (E6 medium).

The MSC differentiation medium is used to culture the trophoblast stem cells to obtain the mesenchymal stem cells. The MSC differentiation medium may include minimum essential medium α (α-MEM) medium, non-essential amino acids (NEAA) cell culture supplement, alanyl-glutamine (GlutaMax) supplement, 2-mercaptoethanol, fetal bovine serum, and human platelet lysate, etc., or any combination thereof. For example, the MSC differentiation medium includes α-MEM medium, 1×NEAA cell culture supplement, 1×GlutaMax supplement, 2-mercaptoethanol, fetal bovine serum, and human platelet lysate. Merely by way of example, the MSC differentiation medium includes α-MEM medium, 1×NEAA cell culture supplement, 1×GlutaMax supplement, 0.1 mM 2-mercaptoethanol, 5% fetal bovine serum, and 5% human platelet lysate.

The MSC expansion medium is used for the passaging culture of the mesenchymal stem cells. In some embodiments, the MSC expansion medium is the same as the MSC differentiation medium. For example, the MSC expansion medium includes α-MEM medium, 1×NEAA cell culture supplement, 1×GlutaMax supplement, 2-mercaptoethanol, fetal bovine serum, and human platelet lysate. The 2-mercaptoethanol may be 0.1 mM 2-mercaptoethanol, the fetal bovine serum may be 5% fetal bovine serum, and the human platelet lysate may be 5% human platelet lysate. In some embodiments, the MSC expansion medium is different from the MSC differentiation medium.

In some embodiments, step b) is performed for a plurality of days. For example, step b) is performed for 1-15 days. As another example, step b) may be performed for 2-10 days. As yet another example, step b) may be performed for 3-9 days. As yet another example, step b) may be performed for 4-8 days. As yet another example, step b) may be performed out 6 days.

In some embodiments, step c) includes subjecting the trophoblast stem cells or the second cell culture to an MSC differentiation culture for a plurality of days to obtain P1 generation cells, and continually subjecting the P1 generation cells to the MSC differentiation culture for a plurality of days to obtain the mesenchymal stem cells or the third cell culture. For example, the trophoblast stem cells or the second cell culture are subjected to the MSC differentiation culture for 1-10 days to obtain the P1 generation cells, and the P1 generation cells continue to be subjected to the MSC differentiation culture for 1-15 days to obtain the mesenchymal stem cells or the third cell culture. As another example, the trophoblast stem cells or the second cell culture are subjected to the MSC differentiation culture for 3-9 days to obtain the P1 generation cells, and the P1 generation cells continue to be subjected to the MSC differentiation culture for 3-12 days to obtain the mesenchymal stem cells or the third cell culture. As yet another example, the trophoblast stem cells or the second cell culture are subjected to the MSC differentiation culture for 5-7 days to obtain the P1 generation cells, and the P1 generation cells continue to be subjected to the MSC differentiation culture for 6-9 days to obtain the mesenchymal stem cells or the third cell culture. As yet another example, the trophoblast stem cells or the second cell culture are subjected to the MSC differentiation culture for 5 or 6 days to obtain the P1 generation cells, and the P1 generation cells continue to be subjected to the MSC differentiation culture for 7 or 8 days to obtain the mesenchymal stem cells or the third cell culture. As yet another example, the trophoblast stem cells or the second cell culture are subjected to the MSC differentiation culture for 5 days to obtain the P1 generation cells, and the P1 generation cells continue to be subjected to the MSC differentiation culture for 7 days to obtain the mesenchymal stem cells or the third cell culture.

In some embodiments, step d) includes subjecting the P1 generation cells to an MSC expansion culture to obtain P2 generation cells, subjecting the P2 generation cells to the MSC expansion culture to obtain P3 generation cells, subjecting the P3 generation cells to the MSC expansion culture to obtain P4 generation cells, and continually subjecting the P4 generation cells to the MSC expansion culture. In some embodiments, a time of each MSC expansion culture is in a range of a certain number of days. For example, the time of each MSC expansion culture is in a range of 1-10 days. As another example, the time of each MSC expansion culture is in a range of 2-8 days. As yet another example, the time of each MSC expansion culture is in a range of 3-5 days. In some embodiments, the time of each MSC expansion culture may be the same or different. For example, the P1 generation cells are subjected to the MSC expansion culture for 5 days to obtain the P2 generation cells, the P2 generation cells are subjected to the MSC expansion culture for 4 days to the P3 generation cells, and the P3 generation cells are subjected to the MSC expansion culture for 3 days to the P4 generation cells. For another example, the time of each MSC expansion culture is 3 days, that is, each MSC expansion culture is performed every 3 days.

In some embodiments, the trophoblast stem cells obtained in step b) are trophoblast stem cells expressing cell surface markers GATA3 and KRT7.

In some embodiments, the mesenchymal stem cells obtained in steps c) and d) are mesenchymal stem cells expressing cell surface markers CD44, CD73, CD90, CD105, and CD166. Correspondingly, in mesenchymal stem cells at a 16th passage (or generation) or later, a proportion of the mesenchymal stem cells expressing cell surface markers CD44, CD73, CD90, CD105, and CD166 is no less than a first proportion. The first proportion may be 80%, 85%, 90%, 95%, 98%, 99%, etc. For example, in the mesenchymal stem cells at the 16th passage or later, the proportion of the mesenchymal stem cells expressing cell surface markers CD44, CD73, CD90, CD105, and CD166 is no less than 95%.

In some embodiments, the mesenchymal stem cells obtained in steps c) and d) are mesenchymal stem cells expressing cell surface markers HLADR, CD34, and CD45. In the mesenchymal stem cells at the 16th passage or later, a proportion of the mesenchymal stem cells expressing cell surface markers HLADR, CD34, and CD45 may be no higher than a second proportion. The second proportion may be 10%, 5%, 4%, 3%, 2%, 1%, etc. For example, in the mesenchymal stem cells at the 16th passage or later, the proportion of the mesenchymal stem cells expressing cell surface markers HLADR, CD34, and CD45 is no higher than 3%.

In some embodiments, the mesenchymal stem cells obtained in steps c) and d) are pluripotent mesenchymal stem cells capable of differentiating into adipocytes, osteocytes, chondrocytes, myocytes, neuronal cells, and cardiomyocytes.

The present disclosure also provides mesenchymal stem cells prepared by the above method.

In accordance with some embodiments of the present disclosure, the mesenchymal stem cells are prepared by using the expanded potential stem cells as starting cells. The obtained mesenchymal stem cells have a fast proliferation rate, a high passaging efficiency, and a multiplication time of about 1.5 days. This solves the problems of the prior art of long induction and differentiation time, long passaging time, and slow cell proliferation. In addition, the cell culture media used in the present disclosure (e.g., the TSC differentiation medium, the MSC differentiation medium, and the MSC expansion medium) are serum-free and xeno-source-free culture systems that prevent contamination by xeno pathogens, thereby addressing safety concerns and improving the quality of the mesenchymal stem cells. Additionally, the differentiation efficiency of the mesenchymal stem cells is improved. The characteristics of the mesenchymal stem cells are maintained over time even after prolonged passaging cultures (e.g., 16 or more passages).

In addition, the mesenchymal stem cells derived from the expanded potential stem cells prepared in the present disclosure have the ability to secrete a higher level of fibroblast growth factor 4 (FGF4), which has a good therapeutic effect for type 2 diabetes. Thus, the mesenchymal stem cells are able to be applied to the preparation of drugs for the treatment of type 2 diabetes or antihyperglycemic drugs.

The following examples are some more specific illustrations associated with some embodiments of the above. A part of elements of these examples may also be replaced or combined with corresponding elements in other examples to form new embodiments. The experimental process in the following examples is conventional if not otherwise stated. The test materials used in the following examples were obtained by purchase from conventional biochemical reagent companies, if not otherwise specified. The quantitative tests in the following examples were set up for three repetitions of the experiment, and the results were averaged. It should be appreciated that the following examples are intended to better explain the present disclosure and are not intended to limit the present disclosure.

The information of reagents referred to in the present disclosure is shown in Table 1.

TABLE 1

Reagent information

| Name | Manufacturer | Item number |
|---|---|---|
| Matrigel | Corning | 354277 |
| IMDM | Thermofisher | 12440053 |
| MEM non-essential amino acids solution (100X)) | Thermo | 11140-050 |
| DMEM/F-12 with HEPES | Thermo | 11330-032 |
| GlutaMAX-I(100X) | Gibco | 35050061 |
| Insulin-transferrin-selenium-X | Gibco | 51500056 |
| L-Ascorbic acid | sigma | A92902 |
| BMP4 | Peprotech | 120-05ET |
| Animal-free recombinant human FGF-basic (154 a.a.) | peprotech | AF-100-18B |
| EGF | sigma | SRP3027 |
| CHIR99021 | StemCell Technologies | 72054 |
| SB431542 | abcam | ab120163 |
| 0.25% Trypsin-EDTA(1X) | Thermo | 25200072 |
| KnockOut ™ serum replacement | ThermoFisher | A3181502 |
| A-83-01 | Selleck | S7692 |
| Valproic acid | Selleck | S3944 |
| Y-27632 2HCL | Selleck | S1049 |
| Helios HPCPLCRL05 serum replacement | HELIOS | HPCPLCRL05 |
| CellMax premium fetal bovine serum | Sai Aomei Cell Technology (Beijing) Co. | SA211.02 |

In some embodiments, flow cytometry is employed to determine the expression of a marker gene in a cell.

Merely by way of example, the flow cytometry is described in terms of a target cell culture including target cells. The target cell culture including the target cells may be the first cell culture including the expanded potential stem cells, the second cell culture including the trophoblast stem cells, and/or the third cell culture including the mesenchymal stem cells. The target cell culture may be placed in a target container. The target container may include a cell culture flask, a culture dish, a beaker, a test tube, an Erlenmeyer flask, etc.

The flow cytometry may include the following steps.

Step (1): aspirate off a supernatant from the target cell culture and add pre-warmed dulbecco's phosphate-buffered saline (DPBS) to wash the target cells twice.

Step (2): add 1 mL TRyple digestion solution to the washed target cell solution in step (1), and digest for 5 minutes at 37° C., during which the cells were blown every 2 minutes.

Step (3): add F-12 medium to the digested target cell solution in step (2) to terminate the digestion, and centrifuge the solution added with F-12 medium at 250 centrifugal force (g) for 5 minutes to remove the supernatant.

Step (4): add 1 mL DPBS to the target cell solution with the supernatant removed in step (3) to wash the target cells once.

Step (5): resuspend the target cells obtained in step (4) using 100 μL DPBS containing 4% fetal bovine serum (FBS).

Step (6): add flow cytometry antibody to the target cells after resuspension in step (5) and incubate the target cells at 4° C. for 30 minutes.

Step (7): centrifuge the target cell solution incubated in step (6) at 250 g to remove the supernatant, and add 1 mL DPBS to wash the target cells three times.

Step (8): resuspend the target cell solution using 200 μL DPBS, and detect the resuspended target cell solution using a flow cytometer.

It should be noted that flow cytometry is only for descriptive convenience and does not limit the present disclosure to the scope of the cited embodiments.

Example 1 Preparation of Expanded Potential Stem Cells (EPSCs) by Differentiation of Induced Pluripotent Stem Cells (iPSCs)

The present disclosure uses iPSCs as the starting cells, and after being cultured in a specific medium, the iPSCs are induced to differentiate into the EPSCs. The used iPSCs may be prepared according to the method described in Chinese patent publication No. CN109913494A (e.g., using the reprogramming factor combinations Oct3/4, Klf4, Sox2, P53, L-Myc, Lin28, RARg, Lrh-1), may be prepared according to the method described in the Chinese patent publication No. CN113462638A (e.g., by using the reprogramming factor combinations OCT4, SOX2, E6, and E7), or may be prepared by using a commercially available reprogramming kit.

The EPSC induction and maintenance medium formulations used in this example are shown in Table 2.

TABLE 2

EPSC induction and maintenance medium formulations

| Reagent Name | Reservoir Concentration | Concentration of use | Volume/Mass | |
|---|---|---|---|---|
| DMEM/F-12 | / | / | 23 | mL |
| Neurobasal culture medium | / | / | 23 | mL |
| GlutaMax supplement | 100× | 1% | 500 | μL |
| NEAA | 100× | 1% | 500 | μL |
| β-Mercaptoehanol | 55 mM | 0.1 mM | 91 | μL |
| B27 supplement | 50× | 0.5× | 500 | μL |
| N2 supplement | 50× | 0.5× | 250 | μL |
| ITS-X | 100× | 1× | 500 | μL |
| serum replacement (KSR) | | 3% | 1.5 | mL |
| L-ascorbic acid 2-phosphate (L-AA-Pi) | 50 mg/mL | 50 μg/mL | 50 | μL |
| Water-soluble vitamin E (Trolox) | 100 mM | 10 μM | 5 | μL |
| human leukemia inhibitory factor (LIF) | 50 μg/mL | 10 ng/mL | 10 | μL |
| (S)-(+)-Dimethindene maleate | 10 mM | 2 μM | 10 | μL |
| Minocycline hydrochloride | 10 mM | 2 μM | 10 | μL |
| CHIR99021 | 10 mM | 1 μM | 5 | μL |
| XAV939 | 10 mM | 2 μM | 10 | μL |
| Y-27632 | 10 mM | 2 μM | 10 | μL |
| GSK126 | 5 mM | 1 μM | 10 | μL |
| Activin A | 200 μg/mL | 40 ng/mL | 10 | μL |

The step of preparing the EPSCs from the iPSCs may include the following steps.

(1) Culture iPSCs in a cell culture flask (e.g., a T25 cell culture flask) containing the first cell culture. Waiting for the growth confluence of iP SCs to reach 70%-80%, the following operations were performed in an ultra-clean bench: using an aspirator to suction off the supernatant from the first cell culture including the iPSCs, and adding pre-warmed DPBS to wash the iPSCs twice. 2 mL pre-warmed Tryple: DPBS (e.g., 1:1) digestion solution was added to digest the iPSCs. The cell culture flask was incubated at 37° C. for 2 minutes, the digestion solution was aspirated, and the digestion was continued at 37° C. for 2 minutes. After tapping the cell culture flask to dislodge the iP SCs, 2 mL DMEM/F-12 medium was added to gently blow the iP SCs, the medium containing the iPSCs was transferred to a 15 mL centrifuge tube and centrifuged at 1000 rpm for 5 minutes to remove the supernatant. 1 mL E8 complete medium containing 10 μM ROCK-i inhibitor was added. After blowing the iP SCs evenly, a portion of iP SCs was taken and diluted 5-fold with trypan blue stain (AP staining) solution for cell counting.

(2) DMEM/F12 was aspirated from the culture dish that was pre-coated with matrigel, newly prepared E8 complete medium containing 10 μM ROCK-i inhibitor was added, and iPSCs were inoculated into the culture dish at a cell density of $1 \times 10^4$ cells/cm$^2$. In some embodiments, it is necessary to gently add the iPSC suspension obtained in step (1) along an uncoated side (not add directly on a coating layer). The culture dish was placed in a thermostatic incubator at a temperature of 37° C. and 5% CO$_2$.

(3) After 24 hours of incubation, the culture dish was removed from the incubator and placed in a biosafety cabinet for the following operations. The old liquid in the culture dish was aspirated and a new pre-warmed complete medium (i.e., E8 complete medium containing 10 μM ROCK-i inhibitor) was added.

(4) The complete medium was refreshed for the cells daily according to step (3).

(5) When the cell confluence of the above cells reached 70-80%, the above cells were passaged, and the passaging operation was the same as steps (1) and (2).

(6) After 10 generations of cell passaging, EPSCs morphology was observed, and P6 generation cells were harvested to detect the expression of EPSC-related markers (e.g., OCT4/KLF4/KLF17/DPPA3/DUX4) using fluorescent quantitative real-time polymerase chain reaction (qRT-PCR). DPPA3 is essential for early embryogenesis and maintenance of pluripotency, EPSCs should have significantly higher DPPA3 expression than iPSCs.

The detection results are shown in FIG. 1, (A) of FIG. 1 shows the morphology images of iPSCs and iPSCs-induced EPSC clones passed for 10 generations; (B) of FIG. 1 shows the AP staining image of EPSCs; and (C) of FIG. 1 shows a gene expression profile graph of KLF17/DPPA3/KLF4/OCT4/DUX4 of EPSCs and iP SCs detected by Q-PCR, where the horizontal coordinate are OCT4, KLF4, KLF17, DPPA3, and DUX4, unitless; and the vertical coordinate are gene expression levels, unitless. As shown in (A) of FIG. 1, the EPSC clone passed for 10 generations has a distinctly bulging morphology and increased edge refractivity. Meanwhile, as shown in (B) of FIG. 1, clear clonal coloration is observed from AP staining. As shown in (C) of FIG. 1, the expression of DPPA3, KLF4, and KLF17 in the cells is at least 3-fold higher than that in the iP SCs, and the expression of OCT4 and DUX4 is not significantly down, indicating that the EPSCs prepared in this example have high pluripotency.

Example 2 Preparation of Mesenchymal Stem Cells (MSCs) from Expanded Potential Stem Cells (EPSCs)

a) EPSCs or a first cell culture that includes EPSCs were provided. In some embodiments, step a) is realized by EPSC passaging.

After the EPSCs growth confluence reached about 70%-80%, the supernatant in the first cell culture was aspirated, and pre-warmed DPBS was added to wash the EPSCs twice. After that, a pre-warmed Tryple digestion solution was added to digest the EPSCs to a single-cell state. The digestion was terminated by the addition of F-12 medium, and a mixed solution with the addition of F-12 medium was centrifuged to remove the supernatant of the mixed solution. Cells after removal of the supernatant were resuspended using 1 mL EPSC medium and the cells were counted.

According to a cell density of $1.0 \times 10^4$/mL, EPSCs were inoculated into six-well plates lined with matrigel in advance, with 2 mL E8 complete medium per well, and placed in a thermostatic incubator at 37° C. with 5% $CO_2$ to culture the cells for 24 hours.

b) EPSCs or the first cell culture were cultured in the TSC differentiation medium to obtain TSCs or the second cell culture including the TSCs, that is, induced differentiation of EPSCs to TSCs (days 1-6).

In the step b), TSC differentiation media were screened and optimized, and three medium experimental groups were set up, namely M1 medium, M2 medium, and M3 medium.

M1 medium was mainly composed of DMEM/F-12 and IMDM at a ratio of 1:1, and also included 0.1 mM 2-mercaptoethanol, 20% KSR, 0.5 μM A8301, 10 ng/ml BMP4, and PD173074.

M2 medium mainly contained DMEM/F-12, 0.1 mM 2-mercaptoethanol, 0.2% fetal bovine serum, 0.3% bovine serum albumin (BSA), 1% ITS-X supplement, 1.5 μg/ml L-AA-pi, 50 ng/ml EGF, 2 μM CHIR99021, 0.5 μM A83-01, 1 μM SB431542, 0.8 mM VPA, and 5 μM Y27632.

M3 medium was mainly composed of E6 medium or DMEM/F-12 and IMDM at a ratio of 1:1, and also included 0.1 mM 2-mercaptoethanol, 20% KSR, 1% ITS-X supplement, 1.5 μg/ml L-AA-pi, 50 ng/ml EGF, 2 M CHIR99021, 0.5 μM A83-01, 1 μM SB431542, 0.8 mM VPA, 5 μM Y27632, and 10 ng/ml BMP4.

After passaging of EPSCs, the old liquid was aspirated and divided into 3 portions, the above three media (namely M1 medium, M2 medium, and M3 medium) were added respectively, and the cells were placed in a thermostatic incubator at 37° C. with 5% $CO_2$ for 6 days.

The medium was changed every 2 days thereafter. On day 6 of induced differentiation, qRT-PCR was performed to detect the expression of TSC-related genes GATA3/KRTF/HCGB/TFAP2C/HLAG induced by the three media to determine the optimal differentiation scheme.

Figure 2:
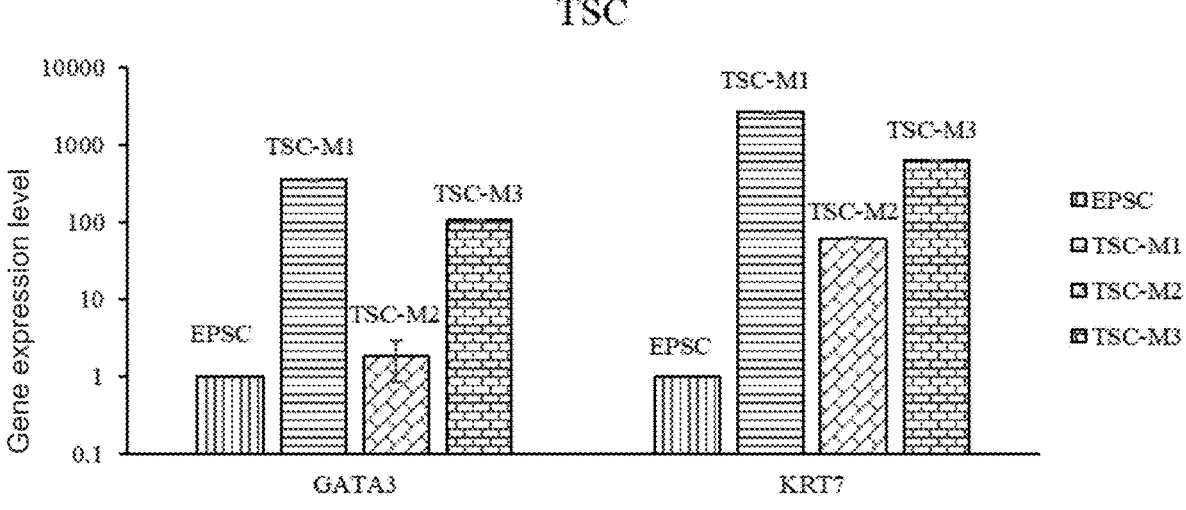
FIG. 2 shows a gene expression profile graph of surface marker genes of trophoblast stem cells after inducing expanded potential stem cells differentiate to trophoblast stem cells by different media according to some embodiments of the present disclosure.

As shown in FIG. 2, TSC-M1 represents the M1 medium-induced culture group, TSC-M2 represents the M2 medium-induced culture group, and TSC-M3 represents the M3 medium-induced culture group; the horizontal coordinates are the genes GATA3 and KRT7, respectively, unitless; the vertical coordinates are the gene expression levels of GATA3 and KRT7, unitless. The TSCs obtained by M1 medium-induced differentiation have the highest expression of genes GATA3/KRT7, and the TSCs obtained by M2 medium-induced differentiation have the lowest expression of genes GATA3/KRT7.

Figure 3:
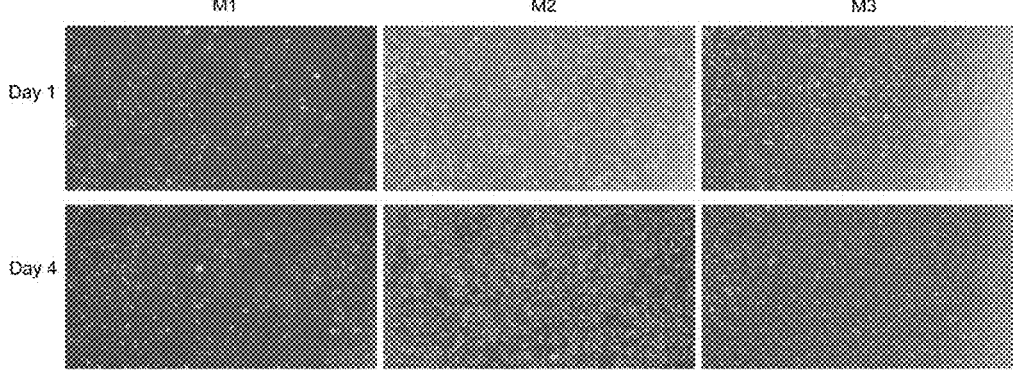
FIG. 3 shows cell morphology images of different media-induced groups on day 1 and day 4 in the process of differentiation of expanded potential stem cells to trophoblast stem cells according to some embodiments of the present disclosure.

As shown in FIG. 3, cell morphology is observed by ordinary light microscopy (magnification 100×) on days 1 and 4 during the differentiation of EPSCs to the TSCs. Cells in the M1 medium-induced differentiation group have abnormal adhesion, and cells that had already been adhered exhibit rounded adhesion and slow cell proliferation, and the morphology of the cells on the day 4 is basically unchanged and the cells basically do not proliferate. Cells in the M2 medium-induced differentiation group and M3 medium-induced differentiation group have normal adhesion on the day 1, and the cells mostly present a short shuttle shape, and the cells proliferate normally on the day 4.

Combining the expression of TSC marker genes, cell morphology, and proliferation, the M3 medium is finally selected as the optimal TSC differentiation medium of the present disclosure, and TSCs (P0 generation) obtained by differentiation induction using M3 medium are used for subsequent experiments.

c) The TSCs or the second cell culture were cultured in an MSC differentiation medium to obtain MSCs or the third cell culture including MSCs, that is, induced differentiation of TSCs to MSCs (days 7-18, P0-P2).

The MSC differentiation medium of step c) may include α-MEM, 1×NEAA, 1×GlutaMax, 0.1 mM 2-mercaptoethanol, 5% fetal bovine serum, and 5% human platelet lysate.

The TSCs in the MSC differentiation medium were digested and passaged, the supernatant was aspirated, and the TSCs were washed twice by adding pre-warmed DPBS. After that, a pre-warmed Tryple digestion solution was added to digest TSCs to a single-cell state. Digestion was terminated by the addition of an F-12 medium, and a mixed solution with the addition of the F-12 medium was centrifuged to remove the supernatant. Cells after removal of the supernatant were resuspended using 1 mL MSC differentiation medium and cells were counted. Cells were inoculated into a culture dish pre-coated with Matrigel at a density of $(1-10) \times 10^4$/cm² and placed in a thermostatic incubator at 37° C. with 5% $CO_2$ for 5 days, at which time the cells were recorded as P1.

When the growth confluence of the P1 generation cells reached approximately 100%, the supernatant was aspirated, and pre-warmed DPBS was added to wash the P1 generation cells twice. After that, a pre-warmed Tryple digestion solution was added to digest the P1 generation cells to a single cell state. Digestion was terminated by the addition of an F-12 medium, and a mixed solution with the addition of the F-12 medium was centrifuged to remove the supernatant. P1 generation cells after removal of the supernatant were resuspended using 1 ml MSC differentiation medium and cells were counted. Cells were inoculated into a culture dish pre-coated with Matrigel at a density of $(1-10) \times 10^4$/cm² and placed in a thermostatic incubator at 37° C. and 5% $CO_2$ for 7 days, at which time the cells were recorded as P2.

Figure 4:
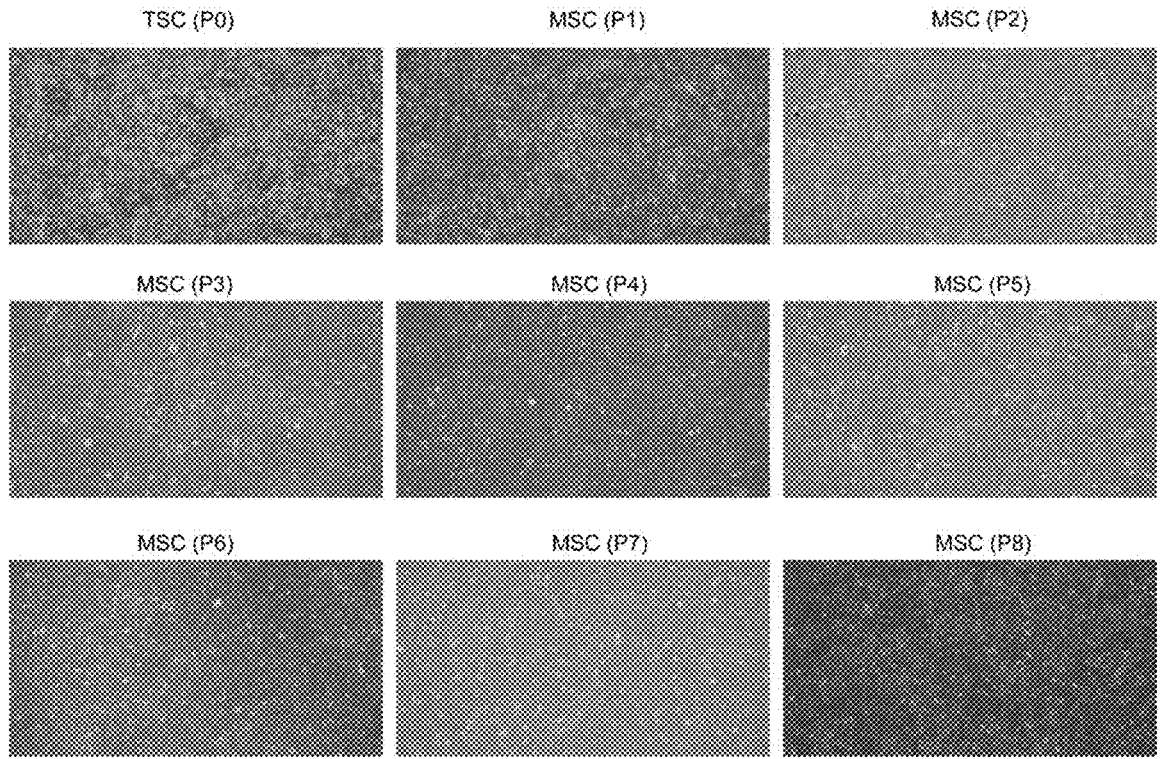
FIG. 4 shows cell morphology images of mesenchymal stem cells and trophoblast stem cells of the first to eighth generation during the process of differentiation of expanded potential stem cells to mesenchymal stem cells according to some embodiments of the present disclosure.

As shown in FIG. 4, under observation by an ordinary light microscope (magnification 100×), the P1 and P2 generation cells present the MSC morphology characteristics of parallel spirals, but the surface marker level of the P1 generation cells does not reach the standard of MSC surface markers, and the surface marker level of the P2 generation cells fully reaches the standard. Therefore, differentiation and culture from TSCs to P2 generation cells can obtain mature and stable MSCs. The process of obtaining MSCs from induced differentiation of TSCs takes 12 days.

d) The MSCs or the third cell culture was placed in an MSC expansion medium for passaging culture while maintaining the characteristics of the MSCs. In some embodiments, step d) is realized by MSC passaging (P2-P8).

Step d) is the process of the expansion and passaging of MSCs. The MSC expansion medium may include α-MEM, 1×NEAA, 1×GlutaMax, 0.1 mM 2-mercaptoethanol, 5% fetal bovine serum, and 5% human platelet lysate. In some embodiments, the MSC expansion medium may be the same or different from the MSC differentiation medium.

When the growth confluence of the P2 generation cells obtained in step c) above reached about 80%-90%, the P2 generation cells were re-digested to single cells. Cells were inoculated into a culture dish pre-coated with Matrigel at a density of $(1-10) \times 10^4$/cm² and placed in a thermostatic incubator at 37° C. with 5% $CO_2$ for 3 days. At this time, the cells were recorded as P3 generation cells, and the P3 generation cells were also collected for flow cytometry to determine the expression of MSC-related marker genes.

Waiting for the growth confluence of the P3 generation cells to reach about 80%-90%, the P3 generation cells were re-digested to single cells. Cells were inoculated into a culture dish pre-coated with gelatin at a density of (1-10)× $10^4$/cm$^2$ and placed in a thermostatic incubator at 37° C. and 5% $CO_2$ for 3 days. At this time, the cells were recorded as P4 generation cells.

Waiting for the growth confluence of the P4 generation cells to reach approximately 80%-90%, the P4 generation cells were re-digested to single cells. Cells were inoculated into a culture dish pre-coated with gelatin at a density of (1-10)×$10^4$/cm$^2$ and placed in a thermostatic incubator at 37° C. and 5% $CO_2$ for 3 days. At this time, the cells are recorded as P5 generation cells.

After the growth confluence of each subsequent generation cells reached about 80%-90%, the cells of that generation were digested and passaged, inoculated into a culture dish pre-coated with gelatin at a density of 0.8×$10^4$-1×$10^4$/cm$^2$, and placed in a thermostatic incubator at 37° C. with 5% $CO_2$.

Figure 5:
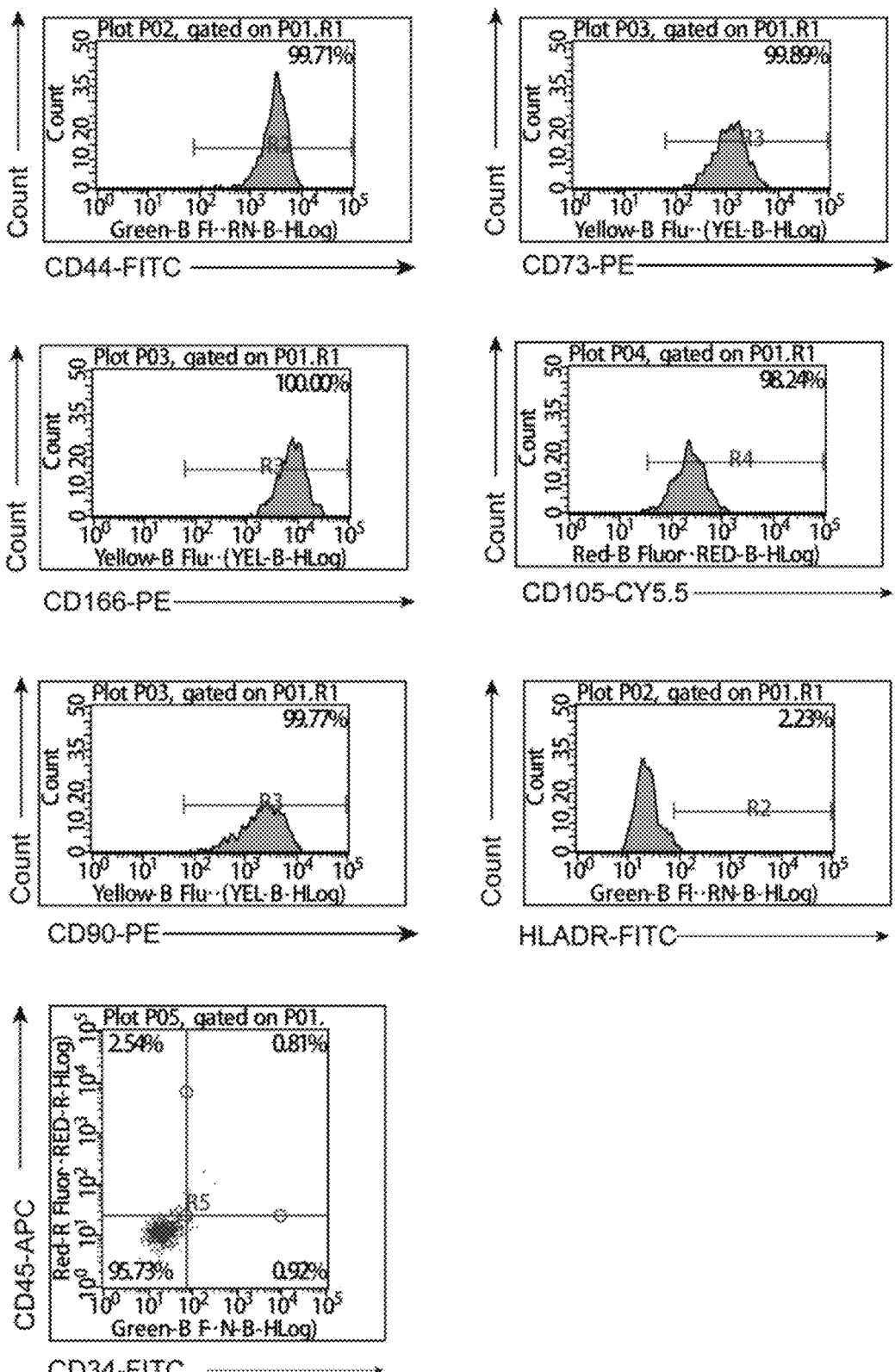
FIG. 5 shows schematic diagrams illustrating flow cytometry results of cell markers for trophoblast stem cells induced and differentiated from expanded potential stem cells according to some embodiments of the present disclosure.

As shown in FIG. 4, after obtaining the P2 generation cells, the cells are passaged every 3 days, and the morphol- Referring to FIG. 5, FIG. 5 shows schematic diagrams illustrating flow cytometry results of cell markers for MSCs (i.e., the P2 generation cells prepared in Example 2) induced and differentiated from the EPSCs. FIG. 5 shows the expression of markers CD44, CD73, CD90, CD105, CD166, HLADR, CD34 and CD45 of MSCs induced and differentiated from the EPSCs. In the flow cytometry, a proportion of MSCs expressing markers CD44, CD73, CD90, CD105, and CD166 should be no less than 95%, and a proportion of MSCs expressing markers HLADR, CD34, and CD45 should be no higher than 3%.

As shown in Table 3 and FIG. 5, a proportion of cells expressing markers CD44 and CD105 in the P1 generation cells is lower than 95%, indicating that the P1 generation cells have not yet differentiated into mature MSCs. In P2 generation MSC cells, a proportion of MSCs expressing markers CD44, CD73, CD90, CD105, and CD166 is greater than 95%, a proportion of MSCs expressing markers HLADR, CD34, and CD45 is less than 3%, indicating that at this time, the cells have fully differentiated into mature MSCs. The P2 generation cells continue to be passaged and expanded to the 16th generation, and the surface markers of MSCs remain at competent levels.

TABLE 3

| Flow cytometry results of surface markers of different generations of MSCs | | | | | | | | |
|---|---|---|---|---|---|---|---|---|
| Cell | Proportion of cell surface markers (%) | | | | | | | |
| generation | CD44 | CD73 | CD90 | CD105 | CD166 | HLADR | CD34 | CD45 |
| P1 | 87.09 | 99.57 | 97.65 | 89.10 | 99.57 | 0.91 | 0.38 | 0.5 |
| P2 | 99.71 | 99.89 | 99.77 | 98.24 | 100.00 | 2.23 | 0.81 | 2.54 |
| P11 | 99.91 | 100 | 97.83 | 99.14 | 99.94 | 0.34 | 1.96 | 2.59 |
| P16 | 99.19 | 99.83 | 97.74 | 99.67 | 99.93 | 0.31 | 1.8 | 2.41 | ogy of the P3 generation and the subsequent passaged cells is observed, the cells of the P3-P11 generations present the MSC morphology characteristics of parallel spirals, no senescence phenomena such as increase in cell volume or slowdown in proliferation are observed, and the cells can proliferate stably.

The expansion is initiated with an inoculated cell count of 720,000, and the cells proliferate to 4.2 million after 4 days of growth, with a calculated doubling time of 38.6 hours (about 1.5 days). It can be seen that the obtained MSCs have a faster proliferation rate.

The cell doubling time may be determined according to equation (1):

$$DT = t * \left[ lg2/(lgNt - lgN0) \right], \qquad (1)$$

Where t is an incubation time, N0 is the number of cells noted for the first time, and Nt is the number of cells after t.

Example 3 Characterization of EPSCs-Derived MSCs

1. Analysis of Surface Markers of MSCs

In order to confirm whether the PSCs-derived MSCs produced by the process of Example 1 have the characteristics of MSCs, surface markers of the P2 generation cells in Example 2 were analyzed using a flow cytometer.

2. Analysis of Tri-Lineage Differentiation Potential in the MSCs

In order to analyze the differentiation potential of MSCs prepared in Example 2, P2 generation MSCs prepared in Example 2 were cultured with osteogenic, lipogenic, and chondrogenic differentiation medium (Biowit), respectively, and the medium was refreshed every 2-3 days. After being cultured for up to 2-3 weeks, the induced adipocytes, osteoblasts, and chondrocytes were identified by oil red O staining, alizarin red staining, and alcian blue staining, respectively.

Figure 6:
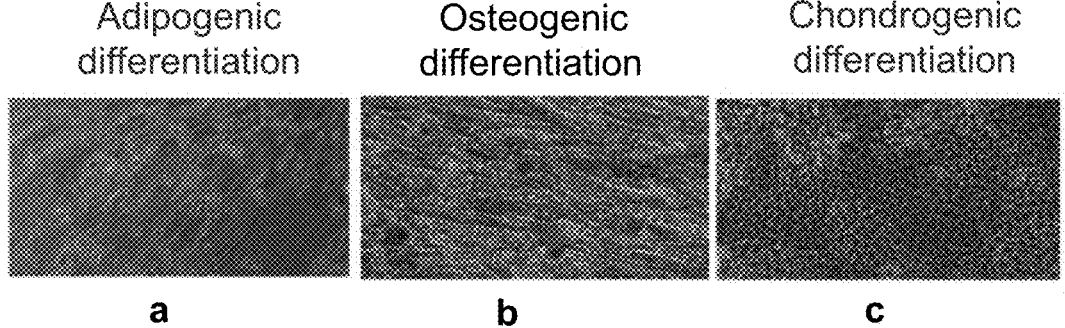
FIG. 6 shows staining identification images of lipogenic differentiation, osteogenic differentiation, and chondrogenic differentiation of trophoblast stem cells induced and differentiated from expanded potential stem cells according to some embodiments of the present disclosure.

In the FIG. 6, a is oil red O staining for identification of adipogenic differentiation (adipocytes); b is alizarin red staining for identification of osteogenic differentiation (osteoblasts); and s c is alcian blue staining for identification of chondrogenic differentiation (chondrocytes). The magnification of the microscope used in FIG. 6 is 100×.

The results are shown in FIG. 6, and the identification of oil red O staining (a in FIG. 6), alizarin red staining (b in FIG. 6), and alcian blue staining (c in FIG. 6) are positive, indicating that the MSCs differentiated from EPSCs prepared in the present disclosure possess the potential to differentiate into adipocytes, osteoblasts, and chondrocytes.

Example 4 Comparison of FGF4 Secretions of Different Sources of MSCs

FGF4 is a member of the fibroblast growth factor (FGF) family, and paracrine FGF4 has antihyperglycemic activity.

Chinese Patent publication CN111944035B discloses FGF4 and its use in the treatment of diabetes mellitus. It was found that FGF4 can exert a hypoglycemic effect by promoting the glucose uptake in muscle and liver, and that FGF4 can directly act on macrophages to block inflammatory responses in liver, muscle and adipose tissue, which in turn enhances insulin sensitivity. Lei Ying et al. (Paracrine FGFs target skeletal muscle to exert potent anti-hyperglycemic effects) discovered that paracrine FGF4 upregulated the cell surface abundance of glucose transporter 4 (GLUT4) in skeletal muscle in an adenosine 5'-monophosphate-activated protein kinase α (AMPKα)-dependent but not insulin-dependent mechanism, thereby exerting its anti-hyperglycemic effect.

MSCs secrete growth factors such as FGF-4, which rapidly induces activation of protein kinase B (AKT), followed by activation of extracellular regulated protein kinase (ERK), which greatly enhances cell proliferation. Thus, this example verifies the proliferative capacity and therapeutic potential in the treatment of type 2 diabetes of the MSCs prepared herein by detecting the amount of FGF4 secreted by MSCs prepared herein, umbilical cord-derived MSCs, dental pulp-derived MSCs, and adipose-derived MSCs.

FGF4 secretion from EPSC-derived MSCs (the P4 generation obtained in Example 2), umbilical cord-derived MSCs, dental pulp-derived MSCs, and adipose-derived MSCs were detected using ELISA kits.

Figure 7:
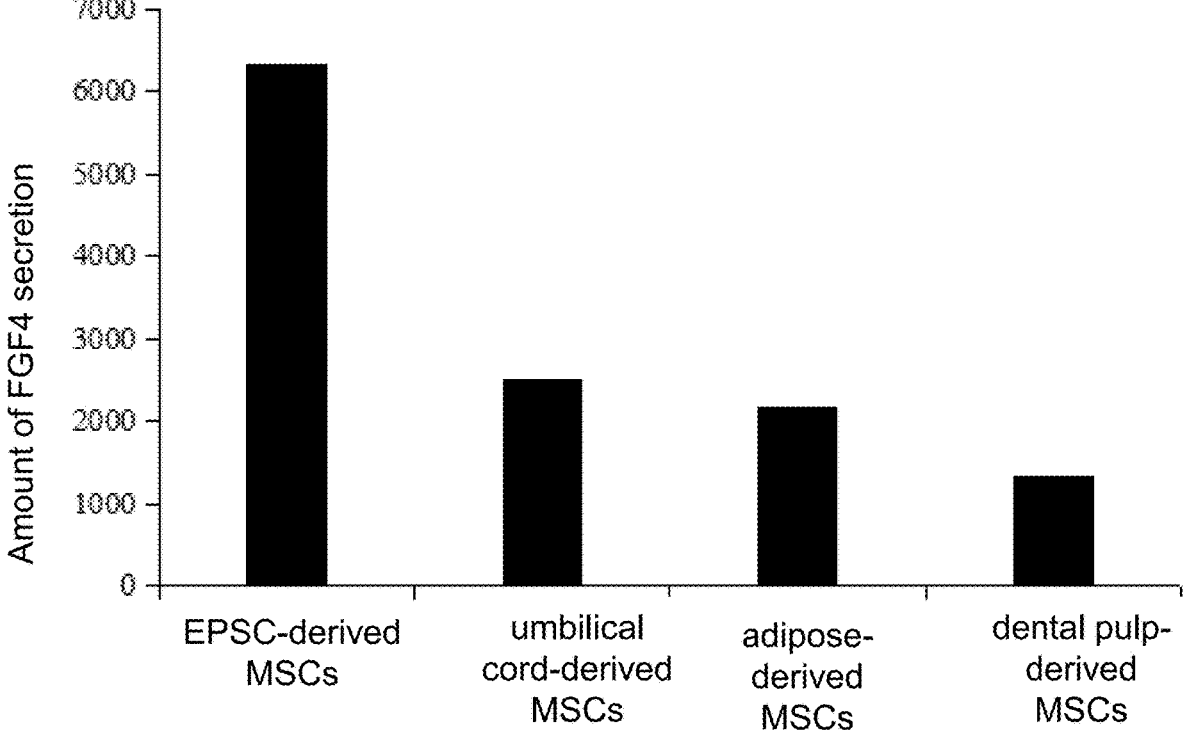
FIG. 7 shows a schematic graph of secretion amounts of fibroblast growth factor 4 (FGF4) of trophoblast stem cells derived from expanded potential stem cells and trophoblast stem cells derived from umbilical cord, dental pulp, and adipose according to some embodiments of the present disclosure.

The results of the ELISA detection for FGF4 secretion from EPSC-derived MSCs (the P4 generation MSCs prepared in Example 2), umbilical cord-derived MSCs, dental pulp-derived MSCs, and adipose-derived MSCs are shown in FIG. 7. The horizontal coordinates are EPSC-derived MSCs, umbilical cord-derived MSCs, adipose-derived MSCs, and dental pulp-derived MSCs, respectively; and the vertical coordinate is the amount of FGF4 secretion with a unit of g/mL. As shown in FIG. 7, the amount of FGF4 secretion of EP SC-derived MSCs (6333 μg/mL) is much higher than that of umbilical cord-derived MSCs (2520 μg/mL), dental pulp-derived MSCs (1341 μg/mL), and adipose-derived MSCs (2186 μg/mL). Thus, it is demonstrated that the MSCs obtained in the present disclosure have great potential in the treatment of type 2 diabetes.

Example 5 Detection of EPSC Residue

EPSC, like iPSC, has the potential to proliferate indefinitely and can form teratomas in vivo. Therefore, to apply EPSC technology to regenerative medicine and provide patients with transplantable cells or tissues, it is important to ensure the safety of the EPSC-derived cells or organs. That is, it must be ensured that undifferentiated EPSCs are excluded from differentiated cells. Thus, the present example validates the safety of MSCs differentiated from EPSCs by detecting residues of undifferentiated EPSCs.

The experiment was divided into 3 groups: a MSCs (the P4 generation cells obtained in Example 2) group, a EPSCs (prepared in Example 1 of the present disclosure) group, and a FBCs (fibroblasts) group. RNA was extracted from the above-mentioned 3 groups of cells and the expression of ESRG, OCT4, Nanog, and SOX2 in the RNA of the 3 groups of cells were detected by qRT-PCR. The detection includes the following steps.

(1) RNA Extraction

Add 500 μL or 1 mL of Trizol reagent depending on the amount of collected cells, blow well to homogenize, and lyse the cells. Add ⅕ volume of phenol-chloroform, shake the mixture well, and place the mixture on ice for 15 minutes. Shake once every 3 minutes. The cooled mixed solution was added to the first centrifuge tube and was centrifuged at 12,000 rpm for 15 minutes at 4° C. The supernatant of the centrifuged mixed solution was taken to a second centrifuge tube, and an equal volume of isopropanol was added to the second centrifuge tube, inverted and mixed. Set aside at −20° C. for 30 minutes. Centrifuge the second centrifuge tube at 12,000 rpm for 15 minutes at 4° C. Pour off the supernatant, add pre-cooled 75% ethanol, and mix well (e.g., after popping up the precipitate in the second centrifuge tube, turn the second centrifuge tube upside down). Centrifuge the second centrifuge tube at 12,000 rpm for 5 minutes at 4° C. to remove the supernatant, and repeat this step once (the repeated step was centrifuging the second centrifuge tube at 12,000 rpm for 5 minutes to remove the supernatant). The precipitate in the second centrifuge tube was dried at 55° C. An RNA solution was obtained by adding an appropriate amount of double distilled $H_2O$ (dd$H_2O$) preheated at 65° C. according to the precipitate size and dissolving the precipitate at 65° C. The RNA concentration of the RNA solution was determined using a Nanodrop spectrophotometer.

(2) Reverse Transcription

Take 1 μg of the prepared RNA sample and perform reverse transcription according to the requirements of the chain reaction-reverse transcription agent (e.g., reverse transcription mix (RT mix)), and the reverse transcription system was as follows:

| Ingredient | Volume |
| --- | --- |
| RNA | 1 μg |
| 4 × RT mix | 4 μL |
| ddH$_2$O | Make up to 16 μL |

The complementary DNA (cDNA) sample was obtained by mixing and centrifuging the above samples, incubating at 45° C. for 15 minutes, and inactivating at 85° C. for 5 minutes. The cDNA sample was diluted 20-fold for subsequent reactions.

(3) Quantitative Real-Time PCR (qRT-PCR)

The samples obtained above were detected by qRT-PCR according to the following system, the reaction system was as follows:

| Ingredient | Volume |
| --- | --- |
| CDNA | 2 μL |
| 2 × SYBR Mix | 10 μL |
| Upstream primer (5 μM) | 1 μL |
| Downstream primer (5 μM) | 1 μL |
| ddH$_2$O | 7 μL |

Figure 8:
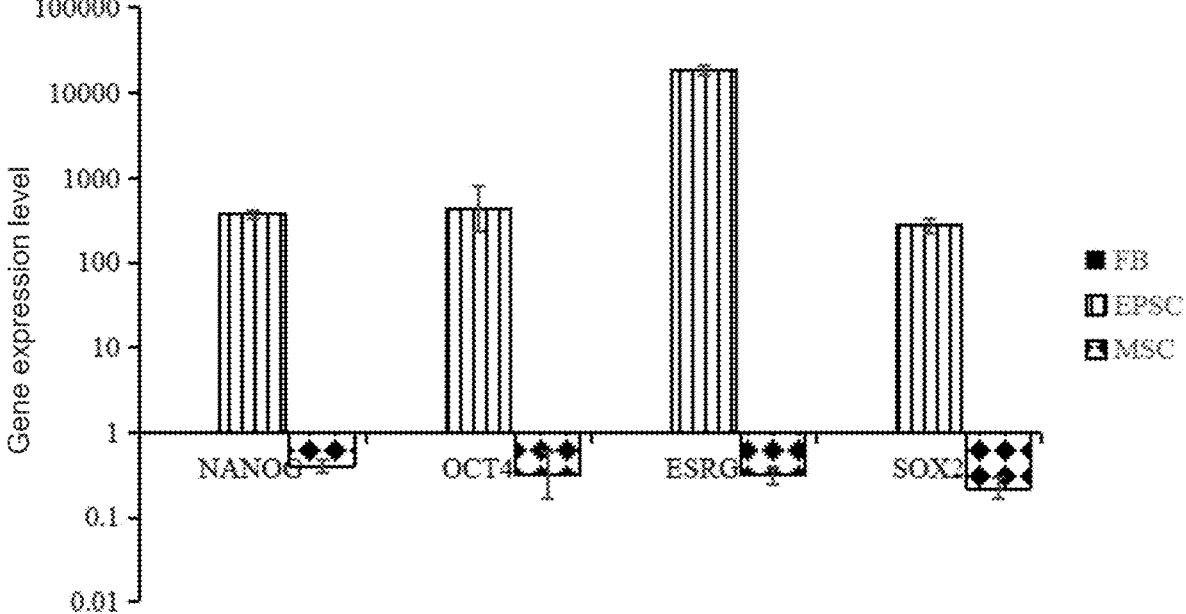
FIG. 8 shows a gene expression profile graph of undifferentiated expanded potential stem cells according to some embodiments of the present disclosure.

The detection results of the undifferentiated EPSC residue are shown in FIG. 8, FB represents fibroblasts, EPSC represents the expanded potential stem cells, and MSC represents the P4 generation MSCs prepared in Example 2; the horizontal coordinates are NANOG, OCT4, ESRG, and SOX2, unitless; and the vertical coordinates are the gene expression levels of NANOG, OCT4, ESRG, and SOX2, unitless. The expression levels of the surface marker genes ESRG, OCT4, Nanog, and SOX2 of the MSCs prepared in the present disclosure are significantly lower than those of the four surface marker genes mentioned above of the EPSCs and fibroblasts. It indicates that there is very little undifferentiated residue of EPSCs in the MSCs prepared from EPSCs differentiation in the present disclosure, which has a high safety.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment," "one embodiment," or "an alternative embodiment" in various portions of this specification are not necessarily all referring to the same embodiment. Furthermore, the particular features, structures, or characteristics may be combined as suitable in one or more embodiments of the present disclosure.

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for preparing mesenchymal stem cells, comprising:
   a) providing expanded potential stem cells or a first cell culture including the expanded potential stem cells;
   b) culturing the expanded potential stem cells or the first cell culture in a trophoblast stem cell (TSC) differentiation medium to obtain trophoblast stem cells or a second cell culture including the trophoblast stem cells, the TSC differentiation medium including a basal medium, 2-mercaptoethanol, serum replacement, insulin-transferrin-selenium-X supplement (ITS-X supplement), L-ascorbic acid-2-phosphate (L-AA-pi), epidermal growth factor (EGF), glycogen synthase kinase 3 beta (GSK3β) receptor inhibitor CHIR99021, anaplastic lymphoma kinase (ALK) 4/5/7 inhibitor A83-01, ALK5 inhibitor SB431542, valproic acid, Rho-associated protein kinase (ROCK) inhibitor Y27632, and bone morphogenetic protein 4 (BMP4), wherein the basal medium is an essential medium or a medium prepared by mixing dulbecco's modified eagle medium/nutrient mixture F-12 (DMEM/F-12 medium) and iscove's modified dubecco's medium (IMDM medium) at a ratio of 1:1;
   c) culturing the trophoblast stem cells or the second cell culture in a mesenchymal stem cell (MSC) differentiation medium to obtain mesenchymal stem cells or a third cell culture including the mesenchymal stem cells, the MSC differentiation medium including minimum essential medium α (α-MEM) medium, 1×non-essential amino acids (1×NEAA) cell culture supplement, 1×alanyl-glutamine (1×GlutaMax) supplement, 2-mercaptoethanol, fetal bovine serum, and human platelet lysate; and
   d) passaging the mesenchymal stem cells or the third cell culture in an MSC expansion medium while maintaining characteristics of the mesenchymal stem cells, the MSC expansion medium including α-MEM medium, 1×NEAA cell culture supplement, 1×GlutaMax supplement, 0.1 mM 2-mercaptoethanol, 5% fetal bovine serum, and 5% human platelet lysate, wherein the mesenchymal stem cells obtained in the step c) and the step d) are mesenchymal stem cells expressing cell surface markers CD44, CD73, CD90, CD105, CD166; and in mesenchymal stem cells at a 16th passage or later, a proportion of the mesenchymal stem cells expressing the cell surface markers CD44, CD73, CD90, CD105, and CD166 is not less than 95%.

2. The method according to claim 1, wherein the step b) is performed for 4-8 days.

3. The method according to claim 2, wherein the step b) is performed for 6 days.

4. The method according to claim 1, wherein the step c) includes: subjecting the trophoblast stem cells or the second cell culture to the MSC differentiation medium for 5-7 days to obtain P1 generation cells, and continually subjecting the P1 generation cells to the MSC differentiation medium for 6-9 days to obtain the mesenchymal stem cells or the third cell culture; and the step d) includes: subjecting the P1 generation cells to the MSC expansion medium to obtain P2 generation cells, subjecting the P2 generation cells to the MSC expansion medium to obtain P3 generation cells, subjecting the P3 generation cells to the MSC expansion medium to obtain P4 generation cells, and continually subjecting the P4 generation cells to the MSC expansion medium every 3 days.

5. The method according to claim 4, wherein the step c) includes: subjecting the trophoblast stem cells or the second cell culture to the MSC differentiation medium for 5 days to obtain the P1 generation cells, and continually subjecting the P1 generation cells to the MSC differentiation medium for 7 days to obtain the mesenchymal stem cells or the third cell culture.

6. The method according to claim 1, wherein the TSC differentiation medium includes the basal medium, 0.1 mM 2-mercaptoethanol, 20% serum replacement, 1% ITS-X supplement, 1.5 μg/ml L-AA-pi, 50 ng/ml EGF, 2 μM CHIR99021, 0.5 μM A83-01, 1 μM SB431542, 0.8 mM valproic acid, 5 μM Y27632, and 10 ng/ml BMP4.

7. The method according to claim 1, wherein the MSC differentiation medium includes the α-MEM medium, the 1×NEAA cell culture supplement, the 1×GlutaMax supplement, 0.1 mM 2-mercaptoethanol, 5% fetal bovine serum, and 5% human platelet lysate.

8. The method according to claim 1, wherein the trophoblast stem cells obtained in the step b) are trophoblast stem cells expressing cell surface markers GATA3 and KRT7.

9. The method according to claim 1, wherein the mesenchymal stem cells obtained in the step c) and the step d) are capable of differentiating into adipocytes, osteocytes, chondrocytes, myocytes, neuronal cells, and cardiomyocytes.

10. The method according to claim 1, wherein the mesenchymal stem cells obtained in the step c) and the step d) are mesenchymal stem cells expressing cell surface markers HLADR, CD34, and CD45; and in mesenchymal stem cells at a 16th passage or later, a proportion of the mesenchymal stem cells expressing the cell surface markers HLADR, CD34, and CD45 is not greater than 3%.

\* \* \* \* \*